(12) United States Patent
Victorovna Likhanova et al.

(10) Patent No.: US 8,821,716 B2
(45) Date of Patent: Sep. 2, 2014

(54) DESULFURIZATION OF HYDROCARBONS BY IONIC LIQUIDS AND PREPARATION OF IONIC LIQUIDS

(75) Inventors: Natalya Victorovna Likhanova, Delegación Gustavo A. Madero (MX); Rafael Martinez Palou, Delegación Gustavo A. Madero (MX); Jorge Froylan Palomeque Santiago, Delegación Gustavo A. Madero (MX)

(73) Assignee: Instituto Mexicano del Petroleo, Mexico City (MX)

( * ) Notice: Subject to any disclaimer, the term of this patent is extended or adjusted under 35 U.S.C. 154(b) by 883 days.

(21) Appl. No.: 12/471,846

(22) Filed: May 26, 2009

(65) Prior Publication Data

US 2009/0288992 A1    Nov. 26, 2009

(30) Foreign Application Priority Data

May 26, 2008    (MX) .................... MX/a/2008/006731

(51) Int. Cl.
| | |
|---|---|
| *C10G 21/20* | (2006.01) |
| *C10G 21/06* | (2006.01) |
| *C10G 21/12* | (2006.01) |
| *C10G 21/16* | (2006.01) |
| *C07D 233/60* | (2006.01) |
| *C10G 21/22* | (2006.01) |
| *C10G 21/18* | (2006.01) |
| *C07D 233/58* | (2006.01) |

(52) U.S. Cl.
CPC ................ *C10G 21/06* (2013.01); *C10G 21/12* (2013.01); *C10G 21/16* (2013.01); *C10G 21/20* (2013.01); *C07D 233/60* (2013.01); *C10G 21/22* (2013.01); *C10G 21/18* (2013.01); *C07D 233/58* (2013.01)
USPC ........ 208/244; 208/208 R; 208/236; 208/237; 208/290; 208/295; 208/298; 546/347; 548/107

(58) Field of Classification Search
USPC .......... 208/208 R, 236, 237, 244, 246, 254 R, 208/290, 295, 296, 298; 546/347; 548/107
See application file for complete search history.

(56) References Cited

U.S. PATENT DOCUMENTS

| | | | |
|---|---|---|---|
| 5,730,860 A | 3/1998 | Irvine | |
| 5,731,101 A * | 3/1998 | Sherif et al. .................. | 429/102 |
| 5,910,440 A | 6/1999 | Grossman et al. | |
| 6,171,478 B1 | 1/2001 | Cabrera et al. | |
| 6,402,940 B1 | 6/2002 | Rappas | |
| 6,406,616 B1 | 6/2002 | Rappas et al. | |
| 6,573,405 B1 * | 6/2003 | Abbott et al. .................. | 564/292 |
| 6,596,130 B2 * | 7/2003 | Westman .................... | 204/157.6 |
| 6,596,914 B2 | 7/2003 | Gore et al. | |
| 6,969,693 B2 * | 11/2005 | Sauvage et al. ............... | 502/159 |
| 7,001,504 B2 * | 2/2006 | Schoonover ................... | 208/236 |
| 7,303,607 B2 * | 12/2007 | Tempel et al. .................. | 95/241 |
| 2002/0035306 A1 | 3/2002 | Gore et al. | |
| 2003/0085156 A1 * | 5/2003 | Schoonover ................... | 208/230 |
| 2004/0045874 A1 | 3/2004 | Olivier-Bourbigou et al. | |
| 2005/0010076 A1 * | 1/2005 | Wasserscheid et al. ........ | 585/862 |
| 2010/0270211 A1 * | 10/2010 | Wolny .......................... | 208/243 |

FOREIGN PATENT DOCUMENTS

| | | | |
|---|---|---|---|
| EP | 1057879 | 12/2000 | |
| KR | 2009098377 A1 * | 9/2009 | ............ C10G 21/20 |
| WO | 0234863 | 5/2002 | |
| WO | 03037835 | 5/2003 | |

OTHER PUBLICATIONS

Ko, et al., "Extractive Desulfurization Using Fe-Containing Ionic Liquids" in Energy & Fuels, 2008, 22, 1687-1690—available on-line Apr. 22, 2008.*
Machine Translation of KR 2009-098377—accessed Aug. 13, 2013.*
Zaczepinski S., Exxon Diesel Oil Deep Desulfurization (DODD), Handbook of Petroleum Refining Processes, 2nd Ed., R.A. Meyers, McGraw-Hill, NY, 1996, Ch. 8.7.
Rogers et al., Petrostar Refining, 217 National Meeting, American Chemical Society, Anaheim, CA, Mar. 1999.
Levy, Unipure Corp., NPRA Meeting No. AM-01-10 Unipure's ASR-2 Diesel Desulfurization Process: A Novel, Cost-Effective Process for Ultra-Low Sulfur Diesel, Mar. 2001.
Avidan et al., Sulphco Corp, NPRA Meeting No. AM-01-55, Sulphco-Desulfurization via Selective Oxidation-Pilot Plant Results and Commercialization, Mar. 2001.
Visser et al., Aqueous Biphasic Systems as a Novel Environmentally-Benign Separations Technology for Metal Ion Removal, The Minerals, Metals & Materials Society, 1999.
Rogers et al., Metal Ion Separations in Room Temperature Ionic Liquids: Potential Replacements for Volatile Organic Diluents, The Minerals, Metals & Materials Society, 1999.
Bosmann et al., Deep Desulfurization of Diesel Fuel by Extraction with Ionic Liquids, Chem. Commun., 2001, 2494-2495.
Huang et al., Desulfurization of Gasoline by Extraction with New Ionic Liquids, Energy & Fuels, 2004, 18, 1862-1864.
Zhang et al., Extractive Desulfurization and Denitrogenation of Fuels Using Ionic Liquids, Ind. Eng. Chem. Res., 2004, 43, 614-622.
Nie et al., Extractive Desulfurization of Fuel Oil Using Alkylimidazole and Its Mixture with Dialkylphosphate Ionic Liquids, Ind. Eng. Chem. Res., 2007, 46, 5108-5112.

(Continued)

*Primary Examiner* — In Suk Bullock
*Assistant Examiner* — Bradley Etherton
(74) *Attorney, Agent, or Firm* — Roylance, Abrams, Berdo & Goodman, L.L.P.

(57) ABSTRACT

The present invention relates to an improved desulfurization process using an ionic liquid compound of general formula $C^+A^-$, where $C^+$ represents an organic cation such as alkyl-pyridinium, di-alkyl imidazolium and tri-alkyl imidazolium; and $A^-$ is an anion of halides of iron (III), such as, for example, $FeCl_4^-$. The desulfurization process is also improved when producing the ionic liquid compound by heating the reactants using microwave energy. The ionic liquids can be used to desulfurize hydrocarbon mixtures by a liquid-liquid extraction.

17 Claims, No Drawings

(56) References Cited

OTHER PUBLICATIONS

Collins et al., Oxidative Desulphurisation of Oils Via Hydrogen Peroxide and Heteropolyanion Catalysis, Journal of Molecular Catalysis A: Chemical, 117 (1997) 397-403.

Babich et al., Science and Technology of Novel Processes for Deep Desulfurization of Oil Refinery Streams: A Review, Fuel 82 (2003) 607-631.

Lo et al., One-Pot Desulfurization of Light Oils by Chemical Oxidation and Solvent Extraction with Room Temperature Ionic Liquids, Green Chemistry, 2003, 5, 639-642.

Visser et al., Room Temperature Ionic Liquids as Replacements for Traditional Organic Solvents and Their Applications Towards "Green Chemistry" in Separation Processes, Green Industrial Applications of Ionic Liquids, Edited by Rogers et al., 2003, 137-156.

Nie et al., Extractive Desulfurization of Gasoline Using Imidazolium-Based Phosphoric Ionic Liquids, Energy & Fuels, 2006, 20, 2083-208.

Planeta et al., Distribution of Sulfur-Containing Aromatics Between [hmim][Tf2N] and supercritical CO2: A Case Study for Deep Desulfurization of Oil Refinery Streams by Extraction with Ionic Liquids, Green Chem., 2006, 8, 70-77.

An et al., Nonhydrodesulfurization Technologies of Light Oil, Progress in Chemistry 19(9): 1331-1344, Sep. 2007.

Holbrey et al., Desulfurisation of Oils Using Ionic Liquids: Selection of Cationic and Anionic Components to Enhance Extraction Efficiency, Green Chem., 2008, 10, 87-92.

\* cited by examiner

US 8,821,716 B2

DESULFURIZATION OF HYDROCARBONS BY IONIC LIQUIDS AND PREPARATION OF IONIC LIQUIDS

CROSS-REFERENCE TO RELATED PATENT APPLICATION

This application claims the priority to Mexican Patent Application No. MX/a/2008/006731, filed on May 26, 2008, in the Mexican Patent Office, the disclosure of which is hereby incorporated by reference in its entirety.

FIELD OF THE INVENTION

This invention provides a process for the synthesis of ionic liquids which can be used for the efficient removal of sulfur compounds from hydrocarbon mixtures. The ionic liquids related are insoluble in hydrocarbons but are able to dissolve aliphatic and aromatic sulfur compounds. Thus, the ionic liquids can be used for removal of sulfur compounds by a liquid-liquid extraction process at room temperature and pressure. The invention is also directed to a process for extracting sulfur from a hydrocarbon liquid by contacting the hydrocarbon with the ionic liquid.

More preferably, this invention is related to the synthesis of ionic liquids with general formula $C^+ A^-$, where $C^+$ is an organic cation preferably but not exclusively alkyl pyridinium, dialkylimidazolium, and trialkylimidazolium, the anion $A^-$ is preferably halogen ferrate (III), particularly $Cl.FeCl_3^-$ and $Br.FeCl_3$. The invention is also directed to the process for the extraction of sulfur-containing compounds, such as sulfur compound that are present in gasoline and Diesel as contaminant obtained in petroleum refining processes by contacting with the ionic liquids.

BACKGROUND OF THE INVENTION

The production of gasoline according with the new European Environmental Standards requires that the refiners to lower the sulfur content in gasoline to values that are lower than 50 ppm since 2005. For example in Germany the content of sulfur in gasoline should be lower than 10 ppm. For the case of USA the content of sulfur is limited to lowest than 80 ppm and with average of 30 ppm. In attention to this claims, PEMEX Refining should be produce gasoline with sulfur content between 15 and 30 ppm for the years 2008-2010.

The classic method used for sulfur removal in Refining Processes is the catalytic Hydrodesulfurization (HDS technology) at high temperature and pressure. This method is very costly process that required drastic operation conditions and it is inefficient to reduce aromatic sulfur compounds especially for Mexican heavy crude oil, so is more reasonable the use of alternative desulfurization process. For increasing the efficiency of HDS process some technology modification are required such as the addition of other catalytic bed, more efficient catalyst, higher temperature and pressures and to reduce LHSV to expense of few processing capacity.

New technologic lines have been develop on in several countries in order to resolve this problem (Zaczepinski, S. Exxon, Diesel Oil Deep Desulfurization (DODD) in Handbook of Petroleum Refining Processes, ed. R. A. Meyer, McGraw-Hill, NY, 1996, Ch. 8.7), i.e.: the absorption of sulfur compounds over solid absorbents, like IRVAD® process (U.S. Pat. No. 5,730,860, dated Mar. 24, 1998) from Black & Veatch Pritchard Inc.; the process S-Zorb® from Phillips Petroleum, the process Haldor Topsoe (EP 1057879, dated Dec. 6, 2000); and the liquid-liquid extraction with volatile organic solvents (Petrostar Refining, 217 National Meeting, American Chemical Society, Anaheim, Calif., March, 1999). An original process is the oxidative desulfurization with different oxidant agents (Unipure Corp., NPRA Meeting No AM-01-10, March 2001; Sulphco Corp, NPRA Meeting No AM-01-55, March 2001; BP Chemicals UK, Journal of Molecular Catalysis A: Chemical (1997) 397-403; UOP LLC, U.S. Pat. No. 6,171,478, dated Jan. 9, 2001; EXXON Research and Engineering Co., U.S. Pat. No. 5,910,440, dated Jun. 8, 1999; U.S. Patent Publication No. 2002/0035306 A1 with publication date of Mar. 21, 2002; U.S. Pat. No. 6,596,914 B2, dated Jul. 22, 2003; U.S. Pat. No. 6,406,616, dated Jun. 18, 2002 and U.S. Pat. No. 6,402,940 B1 dated Jun. 11, 2002; Fuel 82 (2003) 4015; Green Chemistry 5 (2003) 639). Recently the extraction of sulfur-containing compounds using liquid-liquid extraction employing ionic liquids has been welcome by scientific community.

Ionic liquids are known for more than 30 years, but their industrial applications began in the last 10 years (Rogers, R. D.; Seddon, K. R (Eds.), Ionic Liquids: Industrial Applications of Green Chemistry, ACS, Boston, 2002). They are applied as solvents and catalyst in alkylation reactions, polymerization and Diels-Alder cycloaddition. In addition they are employed in electrochemical processes, in supercritical $CO_2$ extraction of aromatic compounds and sulfur compounds in hydrocarbon mixtures. One of the first publications mention the use of ionic liquids for the removal of mercaptans (WO 0234863, dated May 2, 2002). The patented method is based on the use of sodium hydroxide in combination with ionic liquids for the conversion of mercaptans to mercaptures, which were removed using ionic liquids. Peter Wassercheid and coworkers published several papers and patents between 2001 and 2005 about the use of ionic liquids for desulfurization of gasolines (Chem. Comun. (2001) 2494; WO 03037835, with publication date of 2003-05-08; U.S. Publication No. 2005/0010076 A1, published Jan. 13, 2005). In these works the authors employed ionic liquids with $C^+$ being 1,3-dialkylimidazolium or tetralkylammonium, and $A^-$ being tetrachloroaluminates or methanesulfonates. By means of a process with several extractions (up to 8 extractions), high extraction of sulfur compounds were achieved using model gasolines. However these kinds of compounds are air and moisture sensitive and a polymerization reaction was observed during the extraction process. U.S. Patent Publication No. 2003/0085156 A1 published May 8, 2003 and U.S. Pat. No. 7,001,504, dated Feb. 21, 2006, also mention the use of ionic liquids, where $C^+$ is an ammonium o fosfonium and quaternary, $A^-$ being tetrachloroaluminates for the extraction of sulfur from model gasoline. In the paper published in Energy & Fuels 18 (2004) 1862, the use of ionic liquids containing Copper chloride (I) anion with the same application, and in the papers Ind Eng. Chem. Res. 43 (2004) 614 and Ind. Eng. Chem. Res. 46 (2007) 5108-5112) several ionic liquids were evaluated for the extraction of sulfur and nitrogen-containing compounds. More recently, some papers (Energy & Fuels 20 (2006) 2083-2087; Green Chemistry 8 (2006) 70-77; Progress in chemistry 19 (2007) 1331-1344; Green Chemistry 10 (2008) 87-92) also report the use of IL for desulfurization processes. U.S. Patent Publication No. 2004/00445874 A1, published Mar. 11, 2004, discloses a procedure for desulfurization and denitrogenation of hydrocarbons fractions using a wide family of ionic liquids and alkylations agents with high efficiency in some cases.

SUMMARY OF THE INVENTION

The present invention is directed to the use of ionic liquids containing halogens of Fe (III) as an anion for these purposes, where these compounds presented very high efficiency for extracting sulfur-containing compounds from gasoline, turbosin, diesel and other petroleum fractions. Another important and novel aspect of the invention is the use of microwave irradiation for synthesizing the ionic liquids suitable for use as extracting agents (symmetric and non-symmetric compounds) with a corresponding shorter time and higher yields in the synthesis of these ionic liquids compared to the conventional methods of synthesis.

The invention is also directed to a process for extracting sulfur and sulfur compounds from a sulfur-containing hydrocarbon liquid by contacting the hydrocarbon liquid with an ionic liquid of the invention for sufficient time to extract the sulfur and sulfur-containing compounds, and thereafter recovering the hydrocarbon liquid.

The ionic liquids of the invention comprise a heterocyclic cation and an iron (III) halide. The heterocyclic cation is an imidazolium compound having at least one $C_1$-$C_{10}$ alkyl group or alkoxy group where the alkyl group and alkoxy group can be linear, branched, substituted or unsubstituted. The heterocyclic cation can be symmetrical or asymmetrical.

DETAILED DESCRIPTION OF THE INVENTION

This invention relates to the field of the synthesis of new ionic liquids and their application for the desulfurization of hydrocarbon fractions by means a liquid-liquid extraction (ionic liquid-hydrocarbon fraction) method. This removal of sulfur compounds is carried out due to the higher affinity among sulfur-containing compounds and the ionic liquid media with respect to the very low polarity of the hydrocarbon media. By means a vigorous stirring between the low immiscible phases following by phase separation step, the sulfur content in the hydrocarbon phase is considerably reduced.

The Ionic Liquids

The ionic liquids employed in this invention present the general formula $C^+A^-$, where $C^+$ is an organic cation, and $A^-$ is the anion. The cation can be, for example, an alkylpyridinium, alkylimidazolium, dialkylimidazolium, hydroxyalkyl alkyl imidazolium and 1,2,3-trialkylimidazolium, $A^-$ is $FeCl_4^-$ or a derivative thereof.

The ionic liquids of this invention were derived from cations produced from imidazol and pyridine derivatives. The imidazol and pyridine cations can have the following formula:

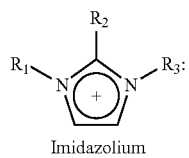
Imidazolium wherein the imidazole nucleus may be substituted with at least one group selected from a linear or branched $C_1$-$C_{10}$ alkyl, a linear or branched $C_1$-$C_{10}$ alkoxy group and functionalized alkyl groups having one heteroatom selected from N, O and S or halogen atoms.

$R_1$, $R_2$, and $R_3$ are independently selected from a group consisting of hydrogen; linear or branched, saturated or unsaturated, aliphatic or alicyclic alkyl groups having from 1 to 10 carbon atoms; a linear or branched alkoxy group or functionalized alkyl groups, having one heteroatom selected from N, O and S or halogen atoms.

The alkyl and alkoxy groups have 1 to 10 carbon atoms, and preferably 2 to 8 carbon atoms. In one embodiment, $R_1$ is a hydrogen or a methyl group. The $R_1$ and $R_3$ groups can be the same to define a symmetrical ionic liquid or different to define an asymmetrical ionic liquid. In another embodiment, $R_1$ is methyl, $R_2$ is a hydrogen or methyl, and $R_3$ is a $C_2$-$C_8$ alkyl. The $R_3$ alkyl group can be a methyl, ethyl, propyl or butyl group. In one preferred embodiment, $R_3$ is a butyl group. The alkyl group can be substituted with a functional group such as a hydroxy group. In one embodiment, $R_3$ is a 2-hydroxyethyl group. In another embodiment, $R_1$ is methyl, $R_2$ is a hydrogen atom or methyl, and $R_3$ is a $C_2$-$C_8$ alkyl which can be substituted or unsubstituted.

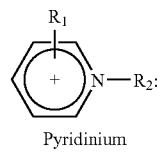
Pyridinium wherein the pyridine nucleus may be substituted with at least one group selected from a linear or branched $C_1$-$C_{10}$ alkyl.

$R_1$, and $R_2$ are independently selected from group consisting of hydrogen; linear or branched, saturated or unsaturated, aliphatic or alicyclic alkyl groups having from 1 to 10 carbon atoms.

In one embodiment, $R_1$ is a hydrogen atom or a alkyl group and $R_2$ is a linear or branched alkyl group. $R_1$ and $R_2$ can be a linear or branched alkyl group having 1 to 10 carbon atoms, and preferably 2 to 8 carbon atoms. In one embodiment, $R_1$ is a hydrogen and $R_2$ is an actyl group. In both cases the anion is of the $FeCl_4^-$ type.

Synthesis of the Ionic Liquids

For non-symmetrical ionic liquids, the synthesis is made in two steps, based on the alkylation method and metathesis of anion, (refs: *Tetrahedron* 2003, 59, 2253-2258;. *New J. Chem.* 2002, 26, 1667-1670; *J. Org. Chem.* 2005, 70, 7882-7891; *Green Chem.* 2003, 5, 181-186; *Inorg. Chem.* 2001, 40, 2298-2304; *J. Chem. Eng. Data* 2006, 51, 691-695). In the first step the following reaction is carried out; and the subsequent reactions, this nomenclature is used:

Nomenclature:
Im=Imidazole
$(CH_3)_3SiNHSi(CH_3)_3$=Hexamethyidisilazane
Im-Si(Me)$_3$=N-(Trimethylsilyl)imidazol
$(CH_3)_3SiNH_2$=Trimethylsilylamine
Cl-Alq=Alkyl chloride
Alq-Im$^+$-Alq Cl$^-$=Dialkyl imidazolium chloride
Alq-Im$^+$-Alq FeCl$_4^-$=Dialkyl imidazolium tetrachloroferrate
HetCic-N=Heterocycle with nitrogen
HetCic-N$^+$-Alq Cl$^-$=Alkyl imidazolium chloride
HetCic-N$^+$-Alq FeCl$_4^-$=Alkyl imidazolium tetrachloroferrate

In the second step the alkyl imidazolium chloride reacted with iron chloride (III), obtaining the ionic liquid with anion $FeCl_4^-$:

The first step of synthesis takes place heating by microwaves irradiation, with which the times of reaction diminish from the 95 to 98%, to comparison with conventional heating synthesis.

In the case of symmetrical ionic liquids, the synthesis is carried out in three steps, based in the method of activation of secondary nitrogen with the trimethylsilyl group, alkylation and metathesis of anion, (refs.: *Polymer* 2004, 45, 5031-5045; *Chem. Commun.* 2001, 1466-1467). In first, the 1-trimethylsilyl derived was synthesized from the nitrogen compound by the following chemical reaction:

Im+(CH$_3$)$_3$SiNHSi(CH$_3$)$_3$ - - - $^\Delta$→Im-Si(Me)$_3$+ (CH$_3$)$_3$SiNH$_2$     I)

In the second step, both nitrogen atoms were alkylated with a alkyl chloride:

Im-Si(Me)$_3$+2Cl-Alq→Alq-Im$^+$-Alq Cl$^-$     II)

And in the third step, the precursor is reacted with FeCl$_3$:

Alq-Im$^+$-Alq Cl$^-$+FeCl$_3$→Alq-Im$^+$-Alq FeCl$_4^-$     III)

Of the same way that for not-symmetrical the ionic liquids, the symmetrical ones are synthesized with the use of the microwaves like nonconventional source of heating, with which the times of reaction is diminish more than 90%, with comparable yields respect to conventional method.

To continuation some examples are described, and are not intended to limit the scope of the present invention.

Example 1

Synthesis of 1-butyl-3-methylimidazolium Tetrachloroferrate ([BMIM]FeCl$_4$)

Step 1: In glass reactor, 1.64 g (20 mmol) of 1-methylimidazole was mixed with 5.55 g (60 mmol) of 1-chlorobutane. After 48 hours of stirring and refluxing with conventional heating, the two-phase mixture was formed. The top layer was decanted off. The residue was washed with ethyl acetate (3×20 ml) and vacuum dried at 90° C. for 5 hours. A viscous colorless liquid was obtained (yield 70%).

Step 2: In glass reactor that is equipped with a magnetic stirring mechanism 0.87 g (5 mmol) of 1-butyl-3-methylimidazolium chloride, obtained from step 1, was introduced and 1.22 g (7.5 mmol) of iron chloride (III) anhydrous was added. The mixture was stirred for 20 minutes at room temperature under an inert atmosphere. A dark red liquid was obtained. The spectroscopic characterizations ($^1$H and $^{13}$C NMR) confirm the following chemical structure:

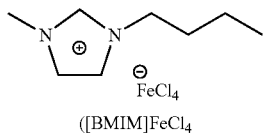

([BMIM]FeCl$_4$

Example 2

Synthesis of 1-butyl-2,3-dimethylimidazolium Tetrachloroferrate ([BDMIM]FeCl$_4$)

Step 1: The 1-butyl-2,3-dimethylimidazolium chloride was obtained (yield 86%) in the same manner described in Example 1 (Step 1) with the exception that 1,2-dimethylimidazole was used instead of 1-methylimidazole.

Step 2: In glass reactor that is equipped with a magnetic stirring mechanism 0.94 g (5 mmol) of 1-butyl-2,3-dimethylimidazolium chloride was introduced and 1.22 g (7.5 mmol) of iron chloride (III) anhydrous was added. The mixture was stirred for 20 minutes at room temperature under an inert atmosphere. A dark red liquid was obtained.

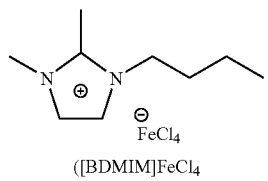

([BDMIM]FeCl$_4$

Example 3

Synthesis of 1,3-dibutylimidazolium Tetrachloroferrate ([DBIM]FeCl$_4$)

This ionic liquid can be obtained by two alternative procedures and using the conventional heating or the microwaves irradiation as the heating source.

Procedure 1

Step 1: The 1,3-dibutylimidazolium chloride was obtained (yield 90%) in the same manner described in Example 1 (Step 1) with the exception that 2.48 g (20 mmol) of 1butylimidazole was used instead of 1-methylimidazole.

Step 2: In a glass reactor equipped with a magnetic stirring mechanism 1.08 g (5 mmol) of 1,3-dibutylimidazolium chloride was introduced and 1.22 g (7.5 mmol) of iron chloride (III) anhydrous was added. The mixture was stirred for 20 minutes at room temperature under an inert atmosphere. A dark red liquid was obtained.

Procedure 2

This procedure consists of three steps.

Step 1 (Synthesis of 1 (trimethylsilyl)-imidazol): In a reactor 1.36 g (20 mmol) of imidazol and 4.85 g (30 mmol) of 1,1,1,3,3,3-hexamethyldisilazane was mixed under an inert atmosphere. The mixture was refluxing for 12 hrs. The reaction formed N-trimethylsilyl-imidazol which was distilled under reduced pressure to afford a viscous colorless liquid (yield 95%).

Step 2 (Synthesis of 1,3-dibutylimidazolium chloride): In a reactor, to a mixture formed by 1.40 g (10 mmol) of N-trimethylsilyl-imidazol obtained previously and 2.78 g (30 mmol) of 1-chlorobutane was added 30 ml of toluene. After 48 hours of stirring and refluxing, the two-phase mixture was formed. The top layer was decanted off. The residue was washed with ethyl acetate (3×20 ml). Removal of the solvent under reduced pressure afforded a viscous colorless liquid (yield 60%)

Step 3: In a glass reactor that is equipped with a magnetic stirring mechanism 1.08 g (5 mmol) of 1,3-dibutylimidazolium chloride was introduced and 1.22 g (7.5 mmol) of iron chloride (III) anhydrous was added. The mixture was stirred for 20 minutes at room temperature under an inert atmosphere. A dark red liquid was obtained.

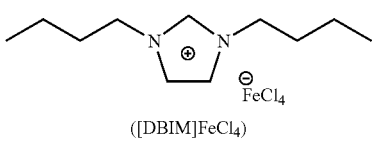

([DBIM]FeCl₄)

The described compound also was synthesized according to the two alternative procedures previously described, but using microwave irradiation (300 W) for 15 minutes of irradiation for step 1 of the first alternative procedure and for 10 minutes and 20 minutes of irradiation for steps 1 and 2 of alternative procedure 2, to obtain the compound in quantitative yields.

Example 4

Synthesis of N-Octylpyridinium Tetrachloroferrate ([OP]FeCl₄)

Step 1: N-octylpyridinium chloride was obtained (yield 68%) in the same manner described in Example 1 (Step 1) with the exception that 1.58 g (20 mmol) of pyridine was used instead of 1-methylimidazole and 8.92 g (60 mmol) of 1-chlorooctane was used instead of 1-chlorobutane Step 2: In a glass reactor equipped with a magnetic stirring mechanism 1.14 g (5 mmol) N-octylpyridinium chloride, obtained from step 1, was introduced and 1.22 g (7.5 mmol) of iron chloride (III) anhydrous was added. The mixture was stirred for 20 minutes at room temperature under an inert atmosphere. A dark red liquid was obtained. The spectroscopic characterizations ($^1$H and $^{13}$C NMR) confirm the following chemical structure:

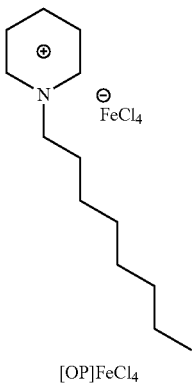

[OP]FeCl₄

Example 5

Synthesis of 1-(2-hydroxyethyl)-3-methylimidazolium Tetrachloroferrate ([HEMIM] FeCl₄)

Step 1: The 1-(2-hydroxyethyl)-3-methylimidazolium chloride was obtained with a 90% yield. In a reactor, to a mixture formed by 11.64 g (20 mmol) of 1-methylimidazole and 3.2 g (40 mmol) 2-chloroethanol was added 30 ml of toluene. After 48 hours of stirring and refluxing, the two-phase mixture was formed. The top layer was decanted off. The residue was washed with ethyl acetate (3×20 ml). Removal of the solvent under reduced pressure afforded a viscous colorless liquid.

Step 2: In a glass reactor equipped with a magnetic stirring mechanism 0.81 g (5 mmol) of 1-(2-hydroxyethyl)-3-methylimidazolium chloride was introduced and 1.22 g (7.5 mmol) of iron chloride (III) anhydrous was added. The mixture was stirred for 20 minutes at room temperature under an inert atmosphere. A dark red liquid was obtained. The spectroscopic characterizations dates ($^1$H and $^{13}$C NMR) confirm the following chemical structure:

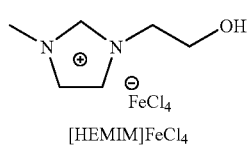

[HEMIM]FeCl₄

Tests of Performance of Ionic Liquids for Desulfurization of Hydrocarbons

The ionic liquids of the invention can be used in a process for extracting sulfur and sulfur compounds from a hydrocarbon liquid by contacting the hydrocarbon liquid with the ionic liquid.

The evaluations were performed with a mixture model prepared through the dissolution of benzothiophene and thiophene in equal parts, in a hexane/heptane mixture (1:1), having a total sulfur concentration of 500 ppm. The extraction tests were done by contacting 1 part of ionic liquid with 5 parts of the mixture model (weight/weight, w/w), in such a way that the extraction process was made with a relation weight of ionic liquid to hydrocarbon. The ionic liquid can be contacted with the hydrocarbon liquid at a ratio of about 1:1 to 1:20 (w/w), and preferably a ratio of about 1:1 to 1:10 (w/w). The determination of the sulfur content was determined by x-ray diffraction.

To 5.0 g of a model mixture (that contained 500 ppm of sulfur) 1.0 g of corresponding ionic liquid was added (obtained from examples 1-5); in the reaction mixture two phases were formed, after 30 min of agitation at room temperature. The ionic liquid phase was separated form the model mixture. In Table 1 are the obtained results.

TABLE 1

Hydrocarbon sulfur removal by extraction with ionic liquids.

| Ionic liquid | Final sulfur content in hydrocarbon (ppm) | % of total removed sulfur in hydrocarbon |
|---|---|---|
| 1* | >10 | 99 |
| 2* | >10 | 99 |
| 3* | 14 | 97 |
| 4* | 152 | 70 |
| 5* | 325 | 35 |

*Notes:
1*: 1-butyl-3-methylimidazolium tetrachloroferrate.
2*: 1-butyl-2,3-dimethylimidazolium tetrachloroferrate.
3*: 1,3-dibutylimidazolium tetrachloroferrate.
4*: N-octylpyridinium tetrachloroferrate.
5*: 1-(2-hydroxyethyl)-3-methylimidazolium tetrachloroferrate.

As observed in Table 1, the ionic liquids with the tetrachloroferrate anion can almost quantitatively remove the sulfur content of the sample original model, especially the ionic liquids with imidazolium cation. Thus, the ionic liquids can be used for the deep desulfurization of hydrocarbon mixtures, such as, gasoline, diesel engine fuel, kerosene, jet fuel and light cyclical oil. While various embodiments have been chosen to illustrate the invention, it will be understood that various changes and modifications can be made without departing from the scope of the invention as recited in the appended claims.

What is claimed is:

1. A process for extracting sulfur and sulfur compounds from a sulfur-containing hydrocarbon liquid comprising the steps of:
   contacting the sulfur-containing hydrocarbon liquid with an ionic liquid of a heterocyclic cation and an iron (III) halide anion for sufficient time for said ionic liquid to extract the sulfur and sulfur compounds from the hydrocarbon liquid, wherein the ionic liquid is symmetrical and the heterocyclic cation has the formula

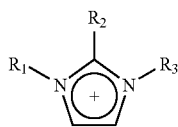

where $R_1$ and $R_3$ are the same and are selected from the group consisting of hydrogen alkyl groups having 1 to 10 carbon atoms; alicyclic alkyl groups having from 1 to 10 carbon atoms; linear or branched $C_1$-$C_{10}$ alkoxy groups and functionalized $C_1$-$C_{10}$ alkyl groups having one heteroatom selected from the group consisting of N, O, S and halogen atoms, $R_2$ is selected from the group consisting of hydrogen; alicyclic alkyl groups having from 1 to 10 carbon atoms; linear or branched $C_1$-$C_{10}$ alkoxy groups and functionalized $C_1$-$C_{10}$ alkyl groups having a heteroatom selected from the group consisting of N, O, S and halogen atoms, and the anion is $FeCl_4^-$; and
   recovering the hydrocarbon liquid.

2. The process of claim 1, wherein the sulfur compounds are selected from the group consisting of thiophenes, benzothiophenes, and mixtures thereof.

3. The process of claim 1, wherein the hydrocarbon liquid is selected from the group consisting of gasoline, diesel fuel, kerosene, jet fuel, and light cyclical oil.

4. The process of claim 3, wherein the ratio of the ionic liquid to the hydrocarbon is about 1:1 to about 1:20 by weight, and where the extracting step is carried out at atmospheric pressure at room temperature for about 1 to 120 minutes.

5. A process for the desulfurization of a hydrocarbon, or mixture of hydrocarbons, the process comprising the steps of:
   a) synthesizing at least one ionic liquid by the steps of reciting either a symmetrical imidazole containing compound or a pyridine containing compound with an alkyl chloride while heating with microwave irradiation, and thereafter mixing with $FeCl_3$ to obtain the ionic liquid;
   b) providing a hydrocarbon, or mixture of hydrocarbons, comprising one or more sulfur impurities that are extractable with an ionic liquid;
   c) exposing the hydrocarbon, or mixture thereof, to at least one of said ionic liquid while agitating at a room temperature, atmospheric pressure and for a period of time sufficient for the ionic liquid to extract at least a portion of the one or more sulfur impurities from the hydrocarbon and to form an at least biphasic mixture with the hydrocarbon, or mixture thereof; and
   d) separating the ionic liquid from the hydrocarbon, or mixture thereof, whereby the amount of one or more sulfur impurities in the hydrocarbon, or mixture thereof, is reduced;
   wherein the ionic liquid is a compound, or a mixture of compounds, of the Formula $C^+A^-$, where the $A^-$ is an iron (III) halide anion; the cation ($C^+$) is selected from the group consisting of symmetrical imidazolium cations wherein the imidazole nucleus is substituted with a group selected from the group consisting of $C_{1-10}$ alkyl, $C_{1-10}$ alkoxy, and functionalized $C_{1-10}$ alkyl groups having a heteroatom selected from the group consisting of N, O, S and halogen, and pyridinium cations, and where the pyridine containing compound has the formula

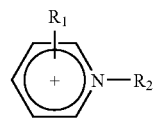

wherein $R_1$ and $R_2$ are independently selected from the group consisting of hydrogen, linear or branched $C_1$-$C_{10}$ alkyl and alicyclic $C_{10}$ alkyl.

6. The process of claim 5, wherein the hydrocarbon is selected from the group consisting of gasoline, diesel, kerosene, jet-fuel fuel and light cycle oil.

7. The process of claim 5, wherein the steps of exposing and separating are repeated.

8. The process of claim 5, wherein the mass ratio of ionic liquid to hydrocarbon, or mixture of hydrocarbons, is in the range of about 1:1 to about 1:20 by weight.

9. The process of claim 5, wherein the sulfur impurities are selected from the group consisting of thiophenes, benzothiophenes, and mixtures thereof.

10. A purified hydrocarbon, or mixture of hydrocarbons, prepared according to the process of claim 5, wherein a hydrocarbon, or mixture thereof, comprising one or more impurities is treated with one or more ionic liquids to provide the purified hydrocarbon, or mixture of hydrocarbons, having a reduced amount of the one or more impurities.

11. The process of claim 5, wherein cation ($C^+$) with the general formula

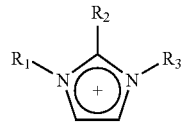

is a symmetrical imidazolium; where $R_1$ and $R_3$ are the same, and are selected from the group consisting of a linear or branched $C_1$ to $C_{10}$ alkyl group, a linear or branched $C_1$ to $C_{10}$ alkoxyl group, and aminoalkyl.

12. The process of claim 5, wherein cation ($C^+$) with the general formula

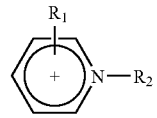

is a pyridinium cation wherein the pyridine nucleus may be substituted with at least one group selected from $C_{1-10}$ linear or branched alkyl; wherein $R_1$ is a hydrogen atom or a $C_1$ to $C_{10}$ linear or branched alkyl group and $R_2$ is a linear or branched $C_1$ to $C_{10}$ alkyl group.

13. The process of claim 5, wherein said ionic liquid is obtained by reacting an imidazole and a silane while heating to obtain a silyl-imidazole with said alkyl chloride.

14. The process of claim 5, wherein said anion $A^-$ is $FeCl_4^-$ and said cation $C^+$ is

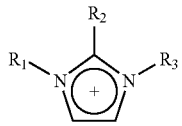

where $R_1$ and $R_3$ are the same, and are selected from the group consisting of an alkyl having 1 to 10 carbon atoms, alicyclic alkyl groups having from 1 to 10 carbon atoms; linear or branched $C_1$-$C_{10}$ alkoxy groups, and $C_1$-$C_{10}$ aminoalkyl groups, and $R_2$ is selected from the group consisting of hydrogen; alicyclic alkyl groups having from 1 to 10 carbon atoms; linear or branched $C_1$-$C_{10}$ alkoxy groups and functionalized alkyl groups having a heteroatom selected from the group consisting of N, O, S and halogen atoms.

15. A process for extracting sulfur and sulfur compounds from a sulfur-containing hydrocarbon liquid comprising the steps of:
    contacting the sulfur-containing hydrocarbon liquid with an ionic liquid of a heterocyclic cation and $FeCl_4^-$ for a time sufficient to extract the sulfur and sulfur compounds, and recovering the hydrocarbon liquid, wherein said heterocyclic cation has the formula

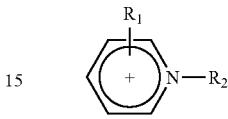

wherein $R_1$ and $R_2$ are independently selected from the group consisting of hydrogen, linear or branched $C_1$-$C_{10}$ alkyl and alicyclic $C_1$-$C_{10}$ alkyl.

16. The process of claim 15, wherein $R_1$ is a hydrogen atom and $R_2$ is a $C_2$ to $C_{10}$ alkyl group.

17. The process of claim 15, wherein $R_1$ and $R_2$ are a $C_2$-$C_8$ linear or branched alkyl.

* * * * *